United States Patent [19]

Johnson

[11] 4,423,276

[45] Dec. 27, 1983

[54] OLEFIN ISOMERIZATION PROCESS

[75] Inventor: Thomas H. Johnson, Houston, Tex.

[73] Assignee: Shell Oil Company, Houston, Tex.

[21] Appl. No.: 444,755

[22] Filed: Nov. 26, 1982

[51] Int. Cl.$^3$ .............................. C07C 5/24; C07C 5/30
[52] U.S. Cl. ...................................... 585/665; 585/670; 502/152
[58] Field of Search .............................. 585/665, 670; 252/431 R

[56] References Cited

U.S. PATENT DOCUMENTS

| 3,131,225 | 4/1964 | Rutkowski et al. | 508/7 |
| 3,173,967 | 3/1965 | Brown | 585/328 |
| 3,988,332 | 10/1976 | Schrock | 585/665 |
| 4,125,567 | 11/1978 | Kidwell et al. | 585/665 |

FOREIGN PATENT DOCUMENTS

| 45-53689 | 5/1970 | Japan | 585/665 |
| 51-3065801 | 11/1976 | Japan | 585/665 |

OTHER PUBLICATIONS

Chemical Abstract, 93: 239562a.
McLain et al., J. Am. Chem. Soc., 101(16), 4558, (1979).
J. Schwartz and J. A. Labinger, "Hydrozirconation: A New Transition Metal Reagent . . . ," Angew. Chem. Int. Ed. Engl., 15(1976), p. 333.
A. H. Klazimga and J. H. Teuben, "Synthesis and Properties . . . ," Journal of Organometallic Chemistry, 157(1978), p. 413.

Primary Examiner—Delbert E. Gantz
Assistant Examiner—A. Pal

[57] ABSTRACT

Internal olefins in the 4 to 30 carbon number range are isomerized to alpha olefins, utilizing cyclopentadienyltantalum compounds in either a catalyst or reagent mode. Under a preferred practice of the process of this invention, internal olefin is contacted with the reagent to form a first complex, alpha olefin is liberated from said first complex upon contact with carbon monoxide to yield a second complex, and reagent is regenerated from said second complex upon contact with water.

14 Claims, No Drawings

OLEFIN ISOMERIZATION PROCESS

BACKGROUND OF THE INVENTION

The present invention relates to a process for the conversion of internal olefins having a carbon number in the range from 4 to about 30 to terminal or alpha-olefins of corresponding carbon number.

Olefins in the $C_4$ to $C_{30}$ range have well recognized commercial utility, for instance, in the synthesis of surfactants, lubricants, and plasticizers. From the standpoint of most recognized uses for the olefins, there is a definite economic incentive for the isomerization of olefins having an internal double bond position to alpha olefins with a terminal double bond.

Thermodynamically, however, isomerization in the reverse direction is favored, and many processes are known for the conversion of alpha olefins to internal olefins.

For the conversion of internal olefins to alpha olefins, U.S. Pat. No. 3,131,225 to A. J. Rutkowski and U.S. Pat. No. 3,173,967 to H. C. Brown describe the use of alkylborane compounds. Amoung the drawbacks to use of this process are relatively high temperatures and long reaction times and difficulties in recovering and recycling active alkylborane.

In the isomerization process of the present invention, use is made of certain cyclopentadienyl compounds of tantalum. J. Schwarz et al have reported (Angew. Chem. Int. Ed. Engl., 15 (1976), p.333) that cyclopentadienyl compounds of zirconium, of the form $Cp_2Zr(H)Cl$, can be applied to olefin isomerization. An alkylzirconium species is formed by reaction of an internal olefin with the $Cp_2Zr(H)Cl$. Subsequent cleavage of this species results in a net isomerization of the internal olefin starting material to alpha olefin. This route suffers substantial disadvantage, however, in the measures which must be taken to liberate the olefin. Schwarz et al found that olefin was not released from the alkylzirconium complex upon heating or upon treatment with another olefin, e.g., ethylene. Isomerized olefin was obtained only through treatment of the alkylzirconium species with trityltetrafluoroborate, a procedure accompanied by substantial conversion of the trityltetrafluoroborate to triphenylmethane by-product.

In U.S. Pat. No. 4,125,567, R. L. Kidwell et al also report that zirconium complexes of the same sort investigated by Schwarz et al can be applied to olefin isomerization. In apparent contradiction to the findings of Schwarz, Kidwell et al disclose that alpha olefin can be liberated from the alkylzirconium species by a treatment for exchange of the bound olefin with another olefin (for example, ethylene) of different carbon skeletal structure. It is suggested that formation of an alkylzirconium species from an internal olefin and subsequent exchange with another olefin results in a net isomerization of internal to alpha olefin. Experiments repeating the work of Kidwell et al have not indicated, however, that the overall process fails to achieve such an isomerization in any significant degree. Under the procedures of U.S. Pat. No. 4,125,567, the cyclopentadienyl-zirconium compound apparently accomplishes a separation of alpha olefins from mixtures with internal olefins, rather than a conversion of internal olefins to alpha olefins.

With specific regard to reagents useful in the process of the present invention, cyclopentadienyl-tantalum compounds are known materials (U.S. Pat. No. 3,288,829 to G. Wilkinson; M. L. H. Green et al, J. Chem. Soc. 4854 (1961); and A. H. Klazinga et al, J. Organometal. Chem., 157 (1978), 413). Such compounds are not known to be recognized for utility in olefin isomerization. The Klazinga publication does report that the reaction between $Cp_2TaCl_2$ and either n-BuMgCl or s-BuMgCl yield the complex $Cp_2Ta(H)$ (1-butene).

SUMMARY OF THE INVENTION

It has now been found that certain cyclopentadienyl compounds of tantalum are useful as reagents for the isomerization of $C_4$ to $C_{30}$ internal olefins to alpha olefins. Unlike related zirconium compounds, complexes of olefins with the tantalum undergo cleavage upon treatment with mild liberating agents to result in the desired net isomerization with respect to double bond position.

In its broadest sense, the invention is a process comprising steps for contacting a compound of the formula $Cp_2TaH_3$, wherein Cp represents an optionally alkyl-substituted cyclopentadienyl, indenyl or fluorenyl radical, with an internal olefin having a carbon number in the range from 4 to about 30 to form an alkyl-tantalum complex, and liberating alpha olefin from said complex.

Preferably liberation of the alpha olefin is accomplished through contact of the complex with a liberating agent. The liberating agent is suitably the same internal olefin which serves as starting material for the isomerization process, in which case the two steps can be accomplished in the same reaction mixture with the $Cp_2TaH_3$ functioning in the nature of a catalyst. Alternatively, use may suitably be made of other liberating agents, for instance, oxygen (or air), hydrogen, carbon monoxide, and olefins other than the process starting material or product, in which case the $Cp_2TaH_3$ compound functions as a reagent. Of particular interest is a process employing a carbon monoxide liberating agent, and comprising as an additional, third step a reaction between the resulting $Cp_2Ta(H)CO$ complex and water to regenerate recycleable $Cp_2TaH_3$.

DESCRIPTION OF THE PREFERRED EMBODIMENTS

The present invention is applicable to the isomerization of any internal mono-olefin having a carbon number in the range from 4 to about 30. The process is most efficiently applied to olefins of the lower carbon numbers, preferably to those in the $C_4$ to $C_{20}$ range, more preferably to those in the $C_4$ to $C_{15}$ range, and most preferably to those in the $C_4$ to $C_{10}$ range. Preference may further be stated for an internal olefin starting material of linear (straight-chain) molecular structure, although branched olefins are suitable. The particular position of the internal double bond in the olefin molecule (i.e., whether at the 2, 3, 4 position, etc, in the carbon chain) is not found to materially influence its suitability as starting material for isomerization under the invention.

A necessary process step in any embodiment of the invention is the contact of the internal olefin with a reagent of the formula $Cp_2TaH_3$, wherein each of the two Cp substituents is an optionally-substituted cyclopentadienyl, idenyl, or fluorenyl radical. Preferably, both of the Cp substituents are cyclopentadienyl radicals of the formula $C_5R_5$, wherein each of the five R moieties individually represents a hydrogen atom or an alkyl group. As examples of such preferred Cp substituents, mention may be made of pentaalkylcyclopentadienyl groups (in which all five R moieties represent the same of different alkyl substituents) such as pentamethylcyclopentadienyl, pentaethylcyclopentadienyl, pentabutylcyclopentadienyl, pentaoctylcyclopentadienyl, ethyltetramethylcyclopentadienyl, diethyltrimethylcyclopentadienyl, methylethylpropylhexyloctylcyclopentadienyl; tetraalkylcyclopentadienyl groups (in which four of the five R moieties represent the same or different alkyl substituents while the fifth represents hydrogen) such as tetramethylcyclopentadienyl, methyltriethylcyclopentadienyl, and methylethyldipentylcyclopentadienyl; trialkylcyclopentadienyl groups (three R moieties represent the same or different alkyl substituents while the remaining two represent hydrogen) such as trimethylcyclopentadienyl, methylethylpropylcyclopentadienyl, and methyldibutylcyclopentadienyl; dialkylcyclopentadienyl groups (two R moieties represent the same or different alkyl substituents while the remaining three represent hydrogen) such as dimethylcyclopentadienyl and ethylbutylcyclopentadienyl; and (mono)alkylcyclopentadienyl groups (four R moieties represent hydrogen while the fifth represents an alkyl substituent) such as methylcyclopentadienyl and heptacyclopentadienyl. The particular alkyl substituents may be positioned at any location and in any order on the carbon ring. Thus, 1-methyl-2-ethyl-3-propylcyclopentadienyl is suitable, as is 1-methyl-3-ethyl-4-propylcyclopentadienyl, and as is 1-methyl-2-propyl-3-ethylcyclopentadienyl. For most applications contemplated for the invention, each alkyl group represented by R in the above formula preferably has no more than about 10, more preferably no more than about 6, and most preferably no more than about 3 carbon atoms. Particularly preferred for use in the invention is the compound trihydridobis($h^5$-cyclopentadienyl)tantalum (V), wherein each R substituent the cyclopentadienyl ring is a hydrogen atom.

The Cp substituent of the compound may also suitably represent an optionally-substituted indenyl radical of the formula $C_9R_7$ or a fluorenyl radical of the formula $C_{13}R_9$. Again, each individual R is suitably a hydrogen atom or an alkyl group, and preferences, as indicated above, may be expressed for an R alkyl group of limited carbon number or for a hydrogen atom.

The $Cp_2TaH_3$ compounds utilized in the invention are known materials. The preparation may be accomplished according to methods described by G. Wilkinson in U.S. Pat. No. 3,288,829 the relevant teachings of which are incorporated herein by this reference. Further discussion of the synthesis of such compounds is provided in a publication by M. L. H. Green et al (J. Chem. Soc. (1961), p.4854). In general, preparation is suitably accomplished by combining (i) a tantalum compound (e.g., a halide salt such as $TaCl_5$), (ii) a substituted or unsubstituted cyclopentadienide salt (e.g., NaCp,LiCp), and (iii) a reducing agent (e.g. $NaBH_4$, $NaAlH_2(OCH_2OCH_3)_2$), in a solvent such as tetrahydrofuran. Yields of the desired $Cp_2TaH_3$ are typically on the order of 5 to 10%.

The tantalum atom of the reagent is considered critical for purposes of the invention. Cyclopentadienyl complexes of zirconium are not found to accomplish isomerization of internal to alpha-olefins under like processing conditions. Likewise, niobium agents of the form $Cp_2NbH_3$ are ineffective for the desired isomerization.

Distinctions between the isomerization performance of the $Cp_2TaH_3$ tantalum compounds for purposes of this invention and analogous zirconium compounds are believed to relate to the stability of the complexes formed upon their reaction with olefin. It is considered to be possible to realize the desired isomerization under the invention because the resulting tantalum complex is less stable than the zirconium complex. Relative instability of the tantalum complex facilitates liberation of the isomerized olefin.

The three hydrogen atoms of the cyclopentadienyltantalum compound (that is, the three hydrogens apart from any which form a part of the Cp radicals) are similarly critical. Replacement of one or more of these hydrogen atoms, for instance, by a halogen, analogous to the cyclopentadienylzirconium compounds of the art, results in a compound not suitable for the isomerization process of the invention.

It is of substantial advantage that the process of the invention achieves isomerization of internal to alpha olefins without producing significant changes in carbon structure of the olefin. The process results in little or no branching in the olefin structure. Similarly, little or no dimerization of olefin is encountered, as is the case, for instance, when olefins are contacted with corresponding niobium compounds.

The cyclopentadienyl-tantalum compound may be applied for isomerization as a catalyst. For instance, contact of the compound with internal olefin under suitable temperature conditions results in conversion to alpha olefin. Internal olefin starting material liberates alpha olefin from a complex previously formed, and at the same time is consumed in the formation of a complex through which it will undergo isomerization. In distinction to the disclosure of U.S. Pat. No. 4,125,567, an exchange between olefin molecules of different carbon skeletal structures is unnecessary. Performance as a catalyst, however, it inherently limited by theromdynamic and equilibrium principles. Accordingly, preference is given to the use of the $Cp_2TaH_3$ as a reagent. In this case, stoichiometric reaction between the reagent and the internal olefin starting material yields an alkyltantalum first complex. Subsequent treatment with liberating agent releases alpha olefin from said first complex. Suitable liberating agents for this purpose are substances which preferentially (relative to the alpha olefin product) ligate or react with the cyclopentadienyltantalum compound. In other words, the displacement of alpha olefin from its complex with the reagent is an exothermic reaction. Examples of preferred liberating agents include oxygen (or air) the oxides of carbon, nitrogen, and sulfur (particularly carbon monoxide), hydrogen, and phosphines (particularly alkyl phosphines such as triethyl phosphine). Most desirably the process includes a further step for regeneration of recycleable $Cp_2TaH_3$ from the products of the alpha olefin liberation step. In this regard it has been found to be of advantage to make use of carbon monoxide as the liberating agent, in a step which yields the complex $Cp_2Ta(H)CO$. Treatment of this carbon monoxide complex with water regenerates $Cp_2TaH_3$. Overall, this three step process embodiment, including steps for olefin complex formation, olefin liberation, and reagent regeneration, in effect superimposes a water gas shift reaction upon the isomerization to give a net exothermic cycle.

For all process embodiments of the invention, formation of the complex between the $Cp_2TaH_3$ compound and the internal olefin is suitably accomplished at temperatures in the range from about 0° to 250° C. Temperatures in the range from about 10° to 200° C. are preferred, while temperatures between about 15° and 150° C. are more preferred and those between about 20° and 100° C. are considered most preferred. The lower temperatures within these ranges are particularly preferred for minimizng isomerization of starting material to olefin of different molecular structure. Similar preferences apply to temperature of the alpha olefin liberation and reagent regeneration steps. Process pressure is not critical, but should be sufficient to maintain olefin starting material and product in the liquid phase. Pressures higher than atmospheric are preferred for alpha olefin liberation when hydrogen is used as the liberation agent.

It is generally of advantage to carry out the process in a solvent for $Cp_2TaH_3$ and its complexes. As examples of preferred solvents, mention may particularly be made of ethers and aromatic hydrocarbons, and more particularly of tetrahydrofuran, benzene, toluene, and xylene. Apart from a requirement that the solvent be essentially inert to other components of the processing mixture, however, the choice of solvent is not critical. The use of a substantial quantity of solvent is often desirable. For instance, with benzene as solvent, $Cp_2TaH_3$ is soluble only to the extent of about 5 percent by volume, and reaction solutions of lesser concentration, e.g., about one percent by volume, are often found to result in the most effective use of the compound.

EXAMPLE 1

The compound trihydridobis($h^5$-cyclopentadienyl)-tantalum (V), of the formula $Cp_2TaH_3$ wherein $C_p$ is an unsubstituted cyclopentadienyl radical, was prepared by the following procedure. To a 1000 ml flask were added 0.18 gram mol of sodium borohydride and 0.53 gram mol of sodium cyclopentadienide in 210 ml tetrahydrofuran solvent. The mixture was cooled to ice bath temperature and 0.06 mol of $TaCl_5$ was added over a period of 30 minutes. After refluxing overnight, the solution was cooled to room temperature, transferred to another flask and evaporated under vacuum to yield a thick paste. The paste was poured into a crystallizing dish and evaporated to dryness to produce a brown solid. After grinding to a fine powder, the solid was sublimed to yield 2.2 g of the desired product, a 10% yield based on tantalum.

EXAMPLE 2

A series of experiments were carried out in accordance with the invention for the conversion of 2-butene to 1-butene using the trihydrobis($h^5$-cyclopentadienyl)-tantalum reagent. In each case about 80 ml (gas volume at standard temperature and pressure) of 2-butene (45% cis-2-butene and 55% trans-2-butene) was mixed (in a flask which had been previously purged with nitrogen to remove air) with 10 ml of a solution containing 10 mg of the $CpTaH_3$ reagent in a benzene, tetrahydrofuran, or xylene solvent. After a reaction of the desired duration, oxygen (air) was bubbled through the mixture to liberate alpha-olefin. Analysis of the product was made by ozonolysis. Isomerization results, in terms of percent of the 2-butene converted to 1-butene under various conditions of reaction temperature and time and with different solvents, are summarized in the following table:

ISOMERIZATION OF 2-BUTENE TO 1-BUTENE

| solvent | temperature (° C.) | conversion (%) time (hours) | | | | | |
|---|---|---|---|---|---|---|---|
| | | 5 | 24 | 29 | 48 | 53 | 72 |
| benzene | 20 | 1 | 4 | 5 | 8 | 8 | 8 |
| benzene | 60 | 1 | 4 | 6 | 9 | 9 | 9 |
| benzene | 100 | 2 | 5 | 6 | 10 | 11 | 11 |
| tetrahydrofuran | 20 | 1 | 5 | 5 | 8 | 9 | 10 |
| tetrahydrofuran | 60 | 1 | 5 | 6 | 10 | 10 | 10 |
| tetrahydrofuran | 100 | 1 | 6 | 7 | 11 | 12 | 12 |
| xylene | 20 | 1 | 5 | 5 | 9 | 9 | 9 |
| xylene | 60 | 1 | 5 | 6 | 8 | 10 | 10 |
| xylene | 100 | 1 | 5 | 6 | 10 | 10 | 10 |

EXAMPLE 3

A series of experiments in accordance with the invention were carried out for the isomerization of trans-5-decene. For each experiment, 60 to 140 milligrams of trihydrobis($h^5$-cyclopentadienyl)tantalum, 10 ml of benzene, and 25 microliters of trans-5-decene were added to an 8-dram vial. After one to four days of reaction at room temperature, the product mixtures were analyzed by ozonolysis. Conversions to 1-decene were on the order of about 5% when reagent quantities exceeded about 100 milligrams. With lesser quantities of the $Cp_2TaH_3$ reagent, results were inconsistent, apparently a result of reagent deactivation by impurities (e.g., oxygen) in the reaction system.

COMPARATIVE EXAMPLE

The compound $Cp_2Zr(C_3H_7)Cl$ was prepared by bubbling propylene through a solution of 3.22 grams (12.5 millimols) of $Cp_2Zr(H)Cl$ in 100 ml of dry, oxygen-free tetrahydrofuran. Propylene was bubbled through the stirred solution at a moderate rate for about two hours, until all solid $Cp_2Zr(H)Cl$ had disappeared. The resulting bright yellow solution was bubbled with nitrogen for 15 minutes to remove unreacted propylene.

An unsuccessful attempt was made to convert internal dodecenes to alpha dodecenes according to the procedures of U.S. Pat. No. 4,125,567 using the CpZr(H)Cl reagent. To the solution prepared as described above were added 2.35 grams of a mixture of internal dodecenes and 15 ml of tetrahydrofuran. The mixture was heated to 80° C. and maintained at that temperature under a flow of nitrogen overnight, then cooled to room temperature. Volume was reduced to 40 ml by evaporating under vacuum and the remaining mixture was transferred to an 83 ml autoclave. The autoclave was pressurized to 12.2 atm at −40° C. by addition of propylene. The stirred autoclave was maintained at 80° C. for 11 hours then cooled to room temperature. Gas chromatographic analysis of the resulting liquid product failed to reveal any 1-dodecene product. This result is consistent with the suggestions of Schwarz et al (Angew. Chem. Int. Ed. Engl., Vol. 15 (1976), no.6, p. 333).

EXAMPLE 4

To exemplify a preferred practice under the invention, in which the $Cp_2TaH_3$ is regenerated, the procedure of Example 3 is followed, substituting carbon monoxide for oxygen as the liberating agent. Conversion of trans-5-decene to 1-decene is again about 5%. Exchange between the carbon monoxide and the alpha olefin yields a complex of the form $Cp_2Ta(H)CO$ from which olefins are separated using standard distillation and/or chromatographic techniques. The Cp$_2$Ta(H)CO is then contacted with water at a temperature of about 50° C. and under alkaline conditions (e.g., with pH adjusted to greater than about 7.5 by addition of a base such as potassium hydroxide) to regenerate Cp$_2$TaH$_3$. The reagent is separated from the regeneration mixture, for example, by drying followed by solvent (e.g., benzene) extraction or, more preferably, by sublimation. Regenerated Cp$_2$TaH$_3$ is recycled to contact with additional internal olefin and the cycle repeated.

In addition to the isomerization of internal alpha olefins, the process of the invention has further been found to effect the isomerization of trans olefins to cis olefins. Advantage can be taken of this aspect of the invention, for example, in the preparation of cis-dialkyl-cyclohexanes via a Diels-Alder reaction involving a cis olefin and an appropriate dienophile. Such structural components are found in terpenes and steroids which have utility in drug and pesticide manufacturing. This aspect of the invention is illustrated in the following example.

EXAMPLE 5

Under the procedures of Example 2, isomerization of trans-2-butene to cis-2-butene was accomplished with results as set out in the following table:

ISOMERIZATION OF TRANS-2-BUTENE TO CIS-2-BUTENE

| solvent | temperature °C. | conversion (%) time (hours) | | | | | |
|---|---|---|---|---|---|---|---|
| | | 5 | 24 | 29 | 48 | 53 | 72 |
| benzene | 20 | 3 | 12 | 15 | 21 | 20 | 13 |
| benzene | 60 | 3 | 15 | 18 | 25 | 23 | 11 |
| benzene | 100 | 4 | 17 | 21 | 25 | 23 | 15 |
| tetrahycrofuran | 20 | 2 | 22 | 24 | 15 | 12 | 5 |
| tetrahydrofuran | 60 | 3 | 26 | 26 | 13 | 10 | 4 |
| tetrahydrofuran | 100 | 3 | 27 | 25 | 13 | 12 | 4 |
| xylene | 20 | 2 | 10 | 10 | 18 | 18 | 16 |
| xylene | 60 | 3 | 10 | 12 | 20 | 20 | 17 |
| xylene | 100 | 3 | 14 | 16 | 23 | 22 | 16 |

I claim as my invention:

1. A process for the isomerization of an internal olefin in the carbon number range from 4 to about 30 to an alpha olefin, which comprises steps for:
   (a) contacting a compound of the formula Cp$_2$TaH$_3$, wherein Cp represents an optionally alkyl-substituted cyclopentadienyl, indenyl, or fluorenyl radical, with the internal olefin to form a complex, and
   (b) liberating alpha olefin from said complex.

2. The process of claim 1, wherein Cp represents an optionally alkyl-substituted cyclopentadienyl radical, and the alkyl substituents of the cyclopentadienyl radical each contain no more than about 10 carbon atoms.

3. The process of claim 2, wherein the alkyl substituents each contain no more than about 3 carbon atoms.

4. The process of claim 1, wherein the compound of the formula Cp$_2$TaH$_3$ is trihydrobis(h$^5$-cyclopentadienyl)tantalum.

5. The process of claim 1, wherein the liberating agent is selected from the group consisting of olefins, phosphines, hydrogen, oxygen, and the oxides of carbon, nitrogen, and sulfur.

6. The process of claim 3, wherein the liberating agent is selected from the group consisting of olefins, phosphines, hydrogen, oxygen, and the oxides of carbon, nitrogen and sulfur.

7. The process of claim 4, wherein the liberating agent is selected from the group consisting of olefins, phosphines, hydrogen, oxygen, and the oxides of carbon, nitrogen and sulfur.

8. The process of claim 1, wherein the liberating agent is an internal olefin.

9. The process of claim 1, wherein the liberating agent is oxygen or an oxide of carbon, nitrogen or sulfur.

10. The process of claim 3, wherein the liberating agent is an internal olefin.

11. The process of claim 3, wherein the liberating agent is oxygen or an oxide of carbon, nitrogen or sulfur.

12. The process of claim 4, wherein the liberating agent is an internal olefin.

13. The process of claim 4, wherein the liberating agent is oxygen or an oxide of carbon, nitrogen or sulfur.

14. A process for the isomerization of an internal olefin in the carbon number range from 4 to about 30 to an alpha olefin, which comprises steps for (a) contacting the internal olefin with a reagent of the formula Cp$_2$TaH$_3$, wherein Cp represents a cyclopentadienyl group or an alkyl-substituted cyclopentadienyl group, to form a first complex, (b) contacting said first complex with carbon monoxide to liberate alpha olefin therefrom and to form a second complex, and (c) contacting said second complex with water to regenerate Cp$_2$TaH$_3$ reagent.

* * * * *